United States Patent
Dietiker (10) Patent No.: US 11,998,298 B2
(45) Date of Patent: Jun. 4, 2024

(54) SYSTEM AND METHOD FOR A WEARABLE VITAL SIGNS MONITOR

(71) Applicant: BIOINTELLISENSE, INC., Golden, CO (US)

(72) Inventor: Thomas Dietiker, Palos Verdes Estates, CA (US)

(73) Assignee: BIOINTELLISENSE, INC., Golden, CO (US)

( * ) Notice: Subject to any disclaimer, the term of this patent is extended or adjusted under 35 U.S.C. 154(b) by 944 days.

(21) Appl. No.: 16/266,442

(22) Filed: Feb. 4, 2019

(65) Prior Publication Data

US 2019/0261859 A1    Aug. 29, 2019

Related U.S. Application Data

(60) Provisional application No. 62/635,332, filed on Feb. 26, 2018.

(51) Int. Cl.
*A61B 5/00* (2006.01)
*A61B 5/01* (2006.01)
(Continued)

(52) U.S. Cl.
CPC .......... *A61B 5/0064* (2013.01); *A61B 5/0006* (2013.01); *A61B 5/0205* (2013.01);
(Continued)

(58) Field of Classification Search
CPC ... A61B 5/0064; A61B 5/0006; A61B 5/0205; A61B 5/02438; A61B 5/1455; A61B 5/681; A61B 5/01
See application file for complete search history.

(56) References Cited

U.S. PATENT DOCUMENTS

| | | |
|---|---|---|
| 3,638,640 A | 2/1972 | Shaw |
| 3,799,672 A | 3/1974 | Vurek |

(Continued)

FOREIGN PATENT DOCUMENTS

| | | |
|---|---|---|
| CN | 101884541 A | 11/2010 |
| CN | 102499694 A | 6/2012 |

(Continued)

OTHER PUBLICATIONS

International Search Report prepared by the U.S. Patent and Trademark Office as International Searching Authority for PCT Intl Patent App. No. PCT/US01/25109; dated Feb. 27, 2002; 4 pages.

(Continued)

*Primary Examiner* — Pascal M Bui Pho
*Assistant Examiner* — Michael Yiming Fang
(74) *Attorney, Agent, or Firm* — Maschoff Brennan (57) ABSTRACT

Novel tools and techniques for wearable device vital signs monitoring are provided. An apparatus system includes a remote device, and a wearable device in communication with the remote device. The wearable device includes a polychromatic light source, a spectral sensor, a processor, and a non-transitory computer readable medium comprising instructions executable by the processor. The wearable device is configured to illuminate, via the polychromatic light source, a perfused tissue of the body of the patient, receive, via the spectral sensor, a resultant signal from the body of the patient, and determine a spectral property of the resultant signal. The wearable device may then determine a vital sign of the patient based, at least in part, on a lookup table and the spectral property of the resultant signal.

17 Claims, 6 Drawing Sheets

(51) Int. Cl.
*A61B 5/0205* (2006.01)
*A61B 5/024* (2006.01)
*A61B 5/1455* (2006.01)
*A61B 5/1495* (2006.01)
*A61B 5/02* (2006.01)

(52) U.S. Cl.
CPC ........ *A61B 5/02438* (2013.01); *A61B 5/1455* (2013.01); *A61B 5/14552* (2013.01); *A61B 5/1495* (2013.01); *A61B 5/681* (2013.01); *A61B 5/0008* (2013.01); *A61B 5/0075* (2013.01); *A61B 5/01* (2013.01); *A61B 5/02* (2013.01); *A61B 5/6802* (2013.01); *A61B 5/6803* (2013.01); *A61B 5/6813* (2013.01); *A61B 5/683* (2013.01); *A61B 5/684* (2013.01); *A61B 2562/0219* (2013.01)

(56) References Cited

U.S. PATENT DOCUMENTS

| | | |
|---|---|---|
| 3,998,550 A | 12/1976 | Konishi et al. |
| 4,603,700 A | 8/1986 | Nichols et al. |
| 4,621,643 A | 11/1986 | New, Jr. et al. |
| 4,653,498 A | 3/1987 | New, Jr. et al. |
| 4,700,708 A | 10/1987 | New, Jr. et al. |
| 4,714,080 A | 12/1987 | Edgar, Jr. et al. |
| 4,770,179 A | 9/1988 | New, Jr. et al. |
| 4,796,636 A | 1/1989 | Branstetter et al. |
| 4,824,242 A | 4/1989 | Frick et al. |
| 4,834,532 A | 5/1989 | Yount |
| 4,867,557 A | 9/1989 | Takatani et al. |
| 4,869,253 A | 9/1989 | Craig, Jr. et al. |
| 4,913,150 A | 4/1990 | Cheung et al. |
| 4,942,877 A | 7/1990 | Sakai et al. |
| 5,058,588 A | 10/1991 | Kaestle |
| 5,111,817 A | 5/1992 | Clark et al. |
| 5,113,861 A | 5/1992 | Rother |
| 5,190,038 A | 3/1993 | Polson et al. |
| 5,216,598 A | 6/1993 | Branstetter et al. |
| 5,218,962 A | 6/1993 | Mannheimer et al. |
| 5,246,002 A | 9/1993 | Prosser |
| 5,259,381 A | 11/1993 | Cheong et al. |
| 5,267,562 A | 12/1993 | Ukawa et al. |
| 5,278,627 A | 1/1994 | Aoyagi et al. |
| 5,279,295 A | 1/1994 | Martens et al. |
| 5,368,224 A | 11/1994 | Richardson et al. |
| 5,377,674 A | 1/1995 | Kuestner |
| 5,398,680 A | 3/1995 | Polson et al. |
| 5,421,329 A | 6/1995 | Casciani et al. |
| 5,448,991 A | 9/1995 | Polson et al. |
| 5,490,505 A | 2/1996 | Diab et al. |
| 5,503,148 A | 4/1996 | Pologe et al. |
| 5,564,417 A | 10/1996 | Chance |
| 5,632,272 A | 5/1997 | Diab et al. |
| 5,645,059 A | 7/1997 | Fein et al. |
| 5,685,299 A | 11/1997 | Diab et al. |
| 5,692,505 A | 12/1997 | Fouts |
| 5,694,930 A | 12/1997 | Pries et al. |
| 5,758,644 A | 6/1998 | Diab et al. |
| 5,779,630 A | 7/1998 | Fein et al. |
| 5,782,756 A | 7/1998 | Mannheimer |
| 5,807,247 A | 9/1998 | Merchant et al. |
| 5,820,550 A | 10/1998 | Polson et al. |
| 5,823,950 A | 10/1998 | Diab et al. |
| 5,827,182 A | 10/1998 | Raley et al. |
| 5,830,137 A | 11/1998 | Scharf |
| 5,841,536 A | 11/1998 | Dimmick |
| 5,842,981 A | 12/1998 | Larsen et al. |
| 5,921,921 A | 7/1999 | Potratz et al. |
| 5,934,277 A | 8/1999 | Mortz |
| 5,987,343 A | 11/1999 | Kinast |
| 5,995,858 A | 11/1999 | Kinast |
| 6,036,642 A | 3/2000 | Diab et al. |
| 6,041,247 A | 3/2000 | Weckstrom et al. |
| 6,044,283 A | 3/2000 | Fein et al. |
| 6,011,986 A | 6/2000 | Diab et al. |
| 6,018,673 A | 6/2000 | Chin et al. |
| 6,081,735 A | 6/2000 | Diab et al. |
| 6,115,621 A | 9/2000 | Chin |
| 6,163,715 A | 12/2000 | Larsen et al. |
| 6,206,830 B1 | 3/2001 | Diab et al. |
| 6,215,295 B1 | 4/2001 | Smith, III |
| 6,226,540 B1 | 5/2001 | Bemreuter |
| 6,230,035 B1 | 5/2001 | Aoyagi et al. |
| 6,181,959 B1 | 6/2001 | Schollerman et al. |
| 6,253,097 B1 | 6/2001 | Aronow et al. |
| 6,263,222 B1 | 6/2001 | Diab et al. |
| 6,272,363 B1 | 8/2001 | Casciani et al. |
| 6,356,774 B1 | 3/2002 | Bernstein et al. |
| 6,501,974 B2 | 12/2002 | Huiku |
| 6,537,225 B1 | 3/2003 | Mills |
| 6,600,940 B1 | 7/2003 | Fein et al. |
| 6,611,320 B1 | 8/2003 | Lindberg et al. |
| 6,628,975 B1 | 9/2003 | Fein et al. |
| 6,667,803 B1 | 12/2003 | Flessland et al. |
| 6,673,596 B1 | 1/2004 | Sayler et al. |
| 6,741,876 B1 | 5/2004 | Scecina et al. |
| 6,889,153 B2 | 5/2005 | Dietiker |
| 7,124,048 B2 | 10/2006 | Dietiker |
| 8,271,063 B2 | 9/2012 | Dietiker |
| 10,485,463 B2 | 11/2019 | Dietiker |
| 2001/0005773 A1 | 6/2001 | Larsen et al. |
| 2001/0020123 A1 | 9/2001 | Diab et al. |
| 2001/0029326 A1 | 10/2001 | Diab et al. |
| 2001/0037059 A1 | 11/2001 | Stone et al. |
| 2002/0082488 A1 | 6/2002 | Al-Ali et al. |
| 2002/0161287 A1 | 10/2002 | Schmitt |
| 2003/0006714 A1 | 1/2003 | Choi |
| 2008/0281174 A1* | 11/2008 | Dietiker ............... A61B 5/6826 600/323 |
| 2010/0081944 A1* | 4/2010 | Baker, Jr. ............... A61B 5/022 600/485 |
| 2010/0130840 A1 | 5/2010 | Isaacson |
| 2010/0331636 A1 | 12/2010 | Hubner |
| 2012/0184832 A1 | 7/2012 | Diab et al. |
| 2013/0018241 A1 | 1/2013 | Bezzerides et al. |
| 2014/0073944 A1 | 3/2014 | Rodriguez-Llorente et al. |
| 2014/0275882 A1 | 9/2014 | Addison et al. |
| 2017/0020443 A1* | 1/2017 | Fein ...................... A61M 21/00 |
| 2017/0311855 A1 | 11/2017 | Dietiker |
| 2018/0014793 A1* | 1/2018 | Bejo-Huerto ...... A61B 5/02438 |
| 2020/0163600 A1 | 5/2020 | Dietiker |

FOREIGN PATENT DOCUMENTS

| | | | |
|---|---|---|---|
| CN | 104019908 A | 9/2014 | |
| CN | 104068865 A | 10/2014 | |
| EP | 0898932 A1 | 3/1999 | |
| EP | 0945100 A1 | 9/1999 | |
| EP | 0992214 A2 | 4/2000 | |
| EP | 1437087 A1 | 7/2004 | |
| WO | WO-2002-014793 A3 | 2/2002 | |
| WO | WO-2016-057042 A1 | 4/2016 | |
| WO | WO-2016-057042 A1 * | 4/2016 | ........... A61B 5/1455 |
| WO | WO-2017009233 A1 * | 1/2017 | ......... A61B 5/14552 |
| WO | WO-2017053925 A1 * | 3/2017 | ........... A61B 5/0002 |
| WO | WO-2019-164676 A1 | 8/2019 | |

OTHER PUBLICATIONS

Mendelson, Yitzhak, (2006) Pulse Oximetry; Worcester Polytechnic Institute; 2006, 18 pages.
EP Patent Application No. 07809605; Extended European Search Report dated Nov. 27, 2009, 8 pages.
International Search Report and Written Opinion prepared by the U.S. Patent and Trademark Office as International Searching Authority for PCT Intl Patent App. No. PCT/US14/60004 dated Jan. 14, 2015, 9 pages.
International Preliminary Report on Patentability prepared by the International Bureau for PCT/US14/60004 dated Apr. 20, 2017, 7 pages.

(56) References Cited

OTHER PUBLICATIONS

EP Patent Application No. 14903626.1; Extended European Search Report dated Apr. 24, 2018, 8 pages.
Sources for Illumination downloaded from https://www.spiedigitallibrary.org/ebooks; dated_Dec. 7, 2018; 7 pages.
International Search Report and Written Opinion prepared by the U.S. Patent and Trademark Office as International Searching Authority for PCT Intl Patent App. No. PCT/US19/17107 dated May 9, 2019, 68 pages.
CN Patent Application No. 2014800837461 First Office Action dated May 28, 2019, 10 pages.
U.S. Appl. No. 16/694,867; New Application filed on Nov. 25, 2019, 69 pages.
PCT Intl Patent App. No. PCT/US19/17107 International Preliminary Report on Patentability, dated Sep. 3, 2020, 8 pages.
European Patent Application No. 19710824.4 Communication pursuant to Rules 161(1) and 162 EPC, dated Oct. 9, 2020, 3 pages.
Canadian Application No. 3,131,501 PCT National Phase Entry, dated Sep. 24, 2021, 1 page.
U.S. Appl. No. 16/694,867; Non-Final Office Action, dated Oct. 4, 2021.
U.S. Appl. No. 16/694,867, Notice of Allowance, dated Feb. 9, 2022, 14 pages.
EP Office Action dated Aug. 11, 2023 as received in Application No. 19710824.4.

\* cited by examiner

SYSTEM AND METHOD FOR A WEARABLE VITAL SIGNS MONITOR

CROSS REFERENCE TO RELATED APPLICATIONS

This application claims priority to U.S. Provisional Patent Application Ser. No. 62/635,332 filed Feb. 26, 2018 by Thomas Dietiker, entitled "System and Method for a Wearable Vital Signs Monitor," the entire disclosure of which is incorporated herein by reference in its entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to medical diagnostic tools, and more particularly, to tools and techniques for wearable vital sign monitors.

BACKGROUND

Monochromatic light sources, often light-emitting diodes (LEDs), are utilized in vital sign monitors to obtain non-invasive measurements of blood components or for use in pulse oximetry. Typically, to obtain accurate measurements utilizing a monochromatic light source, the wavelength of the monochromatic light source must be accurately controlled to determine the amount of monochromatic light absorbed and reflected. Thus, LEDs or other light sources used with conventional processes must meet wavelength tolerances for a respective application, and/or additional signal processing techniques for the associated wavelength.

Moreover, utilizing a conventional monochromatic light source, significant variations arise from the movement of a user, skin pigmentation, and the part of the body from which measurements are obtained, and must be eliminated or reduced. Thus, conventional monochromatic vital sign monitors are limited in implementation and use within wearable devices.

Accordingly, tools and techniques for a wearable vital sign monitor are provided.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Certain embodiments provide tools and techniques for providing real-time and/or on-demand transcription and captioning services. The tools provided by various embodiments include, without limitation, systems, apparatuses, methods, and/or software products. Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible and/or non-transitory computer readable media (such as, to name but a few examples, optical media, magnetic media, and/or the like).

In an aspect, a system for a wearable vital signs monitor is provided. The system may be configured to be worn by a user and determine the vital signs of the user. The measurement of vital signs may include, without limitation, the measurement of blood oxygen saturation (SpO2), heartrate, blood components, and other physiological parameters. In further embodiments, system may provide monitoring and telemedicine functionality to facilitate remote diagnosis, assessment, and treatment by a healthcare provider. The system includes a remote device coupled to a communications network, and a wearable device in communication with the remote device via the communications network, the wearable device configured to be in contact with a body of a patient and determine vital signals of a patient. The wearable device further includes a polychromatic light source, a spectral sensor, a processor, and a non-transitory computer readable medium comprising instructions executable by the processor. The instructions may be executable by the processor to illuminate, via the polychromatic light source, a perfused tissue of the body of the patient, receive, via the spectral sensor, a resultant signal from the body of the patient, determine a context for the resultant signal, wherein the context is indicative of an area of the body of the patient illuminated by the polychromatic light source, adjust at least one value of a lookup table based at least in part on the context, and determine a vital sign of the patient based, at least in part, on a value of the resultant signal and the lookup table as adjusted.

In another aspect, an apparatus for vital signs monitoring is provided. The apparatus may include a polychromatic light source, a spectral sensor, a processor, and a non-transitory computer readable medium comprising instructions executable by the processor. The instructions may be executable by the processor to illuminate, via the polychromatic light source, a perfused tissue of a body of a patient, receive, via the spectral sensor, a resultant signal from the body of the patient, and determine spectral properties of the resultant signal as measured by the spectral sensor, wherein spectral properties include a light power measurement of at least one wavelength. The instructions may then be executed by the processor to determine a vital sign of the patient based, at least in part, on a lookup table and the spectral property of the resultant signal, wherein the lookup table is indicative of a value of the vital sign.

In a further aspect, a method of using a wearable device for vital signs monitoring is provided. The method includes illuminating, via a wearable device, a perfused tissue of a body of a patient with a polychromatic light source. The method further includes receiving, via a spectral sensor of the wearable device, a resultant signal from the body of the patient. The method continues by determining, via an on-board computer of the wearable device, spectral properties of the resultant signal, wherein spectral properties include a light power measurement of at least one wavelength, and determining, via the on-board computer of the wearable device, a vital sign of the patient based, at least in part, on a lookup table and the spectral property of the resultant signal, wherein the lookup table is indicative of a value of the vital sign.

Figure 1:
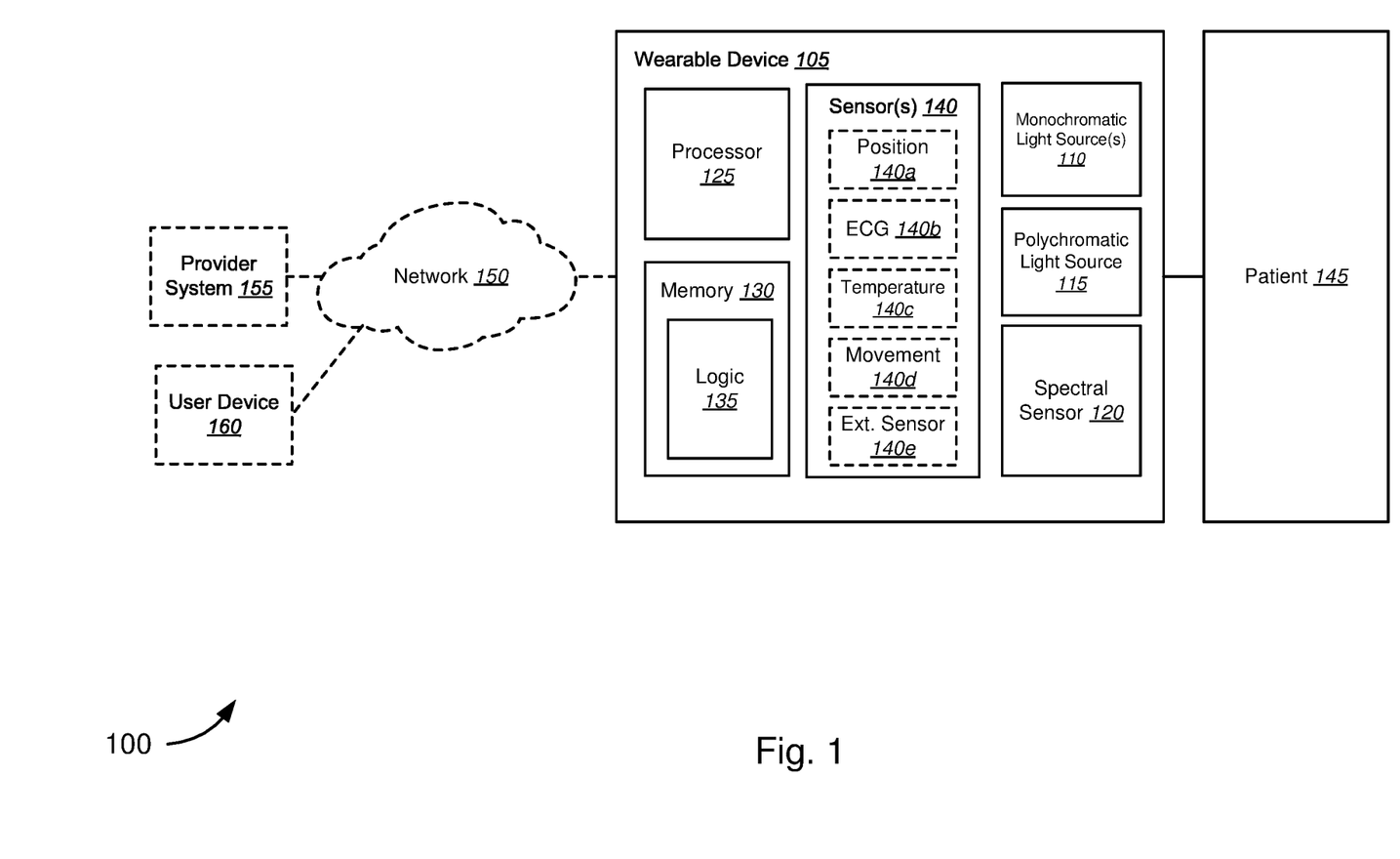
FIG. 1 is a block diagram illustrating a system for a wearable vital signs monitor, in accordance with various embodiments.

FIG. 1 is a block diagram of a system 100 for a wearable vital signs monitor. The system 100 may include a wearable device 105 including one or more monochromatic light sources 110, such as red & infrared (IR) LEDs, a polychromatic light source 115, such as a white LED, a photodetector such as spectral sensor 120, sensors 140, a processor 125, system memory 130 and logic 135. The system may further include a network 150, and remote systems such as a provider system 155 or user device 160.

Sensors 140 of the wearable device 105 may include, without limitation, a position sensor 140a, electrocardiogram (ECG) sensor 140b, temperature sensor 140c, movement sensor 140d, and external sensor 140e. The optional sensors 140 may further include, without limitation, gyroscopes, accelerometer, blood pressure sensors and/or monitors, blood sugar monitors, weight sensors (e.g., scales, load sensors, etc.), magnetometer, camera, global positioning system (GPS) receiver, microphone, Bluetooth sensor (e.g., transmitter, receiver, positional sensor, etc.), or infrared (IR) sensor (e.g., transmitter, receiver, positional sensor, etc.).

It should be noted that the components of the system 100 are schematically illustrated in FIG. 1, and that a variety of hardware configurations are possible in accordance with various embodiments.

In various embodiments, the wearable device 105 may be coupled to a patient 145. The wearable device 105 may be positioned such that the one or more monochromatic light sources 110, polychromatic light source 115, and spectral sensor 120 are in contact or close proximity with the skin of the patient 145. Thus, in various embodiments, the one or more monochromatic light sources 110, polychromatic light source 115, and spectral sensor 120 may be operably coupled to the patient 145. The wearable device 105 may further be coupled to a provider system 155 or another remote device, such as a user device 160, via the network 150. Accordingly, in some embodiments, the wearable device 105 may further include a communications subsystem configured to communicate over the network 150.

In various embodiments, the processor 125, memory 130 and associated logic 135, one or more monochromatic light sources 110, polychromatic light source 115, spectral sensor 120, and sensors 140 may be part of a vital signs monitor assembly of the wearable device 105. An example of a vital signs monitor assembly may include the self-calibrating sensor system, as described in U.S. patent application Ser. No. 15/517,477 (the '477 application) filed Oct. 10, 2014 by Thomas Dietiker, entitled "System and Method for a Non-invasive Medical Sensor." The disclosures of this application are incorporated herein by reference in its entirety for all purposes.

In various embodiments, the one or more monochromatic light sources 110 may include one or more light sources configured to generate light in a respective wavelength. For example, the one or more monochromatic light sources 110 may include, without limitation, a red LED, infrared (IR) LED, or both red & IR LEDs. As will be appreciated by those skilled in the art, although described as generating light at a singular wavelength, in some practical applications, the one or more monochromatic light sources 110 may generate light over a narrow range of wavelengths (e.g., narrow bandwidth) corresponding to a single color of light. For example, the one or more monochromatic light sources 110 may include a red LED configured to emit light at a wavelength of 660 nm, and in some embodiments, within a range of +/−12 nm. In some examples, the one or more monochromatic light sources 110 may include an IR LED configured to emit light at a wavelength of 880 nm, within a range of +/−25 nm. In various embodiments, the polychromatic light source 115 may include any light source, or combination of multiple light sources, configured to generate light in more than one wavelength (e.g., two or more wavelengths, three or more wavelengths, etc.). In various embodiments, the polychromatic light source 115 may include, without limitation, one or more broadband light sources, such as a white LED as described, a combination of two or more monochromatic light sources (e.g., a red, green, and blue (RGB) LEDs), or other combinations of polychromatic and/or monochromatic light sources (e.g., a combination of white LEDs and RGB LEDs). As will be appreciated by those skilled in the art, unlike the one or more monochromatic light sources 110, a polychromatic light source 115 may generate light over a broad range of wavelengths (e.g., broad bandwidth and/or full-spectrum), or alternatively, generate light over multiple ranges of wavelengths corresponding to two or more colors of light. For example, a polychromatic light source 115 may include a light source that emits light over a range of wavelengths in the visible spectrum, ultraviolet (UV), near-IR, and IR. In one example, a polychromatic light source 115 may include a light source that emits light in the range of 200 nm to 2000 nm, or one or more portions of the spectrum from 200 nm to 2000 nm.

In various embodiments, the wearable device 105 may further optionally include one or more sensors 140. The one or more sensors 140 may include, without limitation, a position sensor 140, ECG sensor 140*b*, temperature sensor 140*c*, movement sensor 140*d*, and an external sensor 140*e*. Suitable position sensors 140 may include, without limitation, a gyroscope, Bluetooth-based positional sensor, an accelerometer, or a combination of sensors. Temperature sensors 140*c* may include, without limitation, a thermometer (e.g., resistance thermometer, IR thermometer), thermistor, thermocouple, or other suitable temperature sensors as known to those skilled in the art. Movement sensors 140*d* may include motion detectors (e.g., acoustic, IR, microwave, ultrasonic, video, etc.), accelerometers, among other sensors suitable for detecting movement of the wearable device. The external sensor 140*e* may include any further external sensor that may be coupled to the wearable device 105. For example, external sensor 140*e* may include, without limitation, an additional ECG sensor with an extended lead, a camera, microphone, or any other sensor configured to monitor a patient 145. Accordingly, in various embodiments, the wearable device 105 may further include an interface configured to allow the external sensor 140*e* to be operatively coupled to wearable device 105.

Accordingly, the wearable device 105 may, in some embodiments, include an on-board computer device. For example, the processor 125, memory 130, and logic 135 may be implemented, for example, as part of a programmable logic controller (PLC), single board computer, field programmable gate arrays (FPGA), application specific integrated circuits (ASIC), or a system on a chip (SoC). In various embodiments, the on-board computer, including the processor 125, memory 130, and logic 135, may be configured to perform signal processing and analysis based on signals received from the spectral sensor 120 and/or one or more sensors 140. In further embodiments, at least part of the signal processing and analysis of the signals from the spectral sensor 120 and/or the one or more sensors 140 may be performed by an external computer device, such as one or more desktop computer systems, server computers, and/or dedicated custom hardware appliances, with which the wearable device 105 may be configured to communicate.

In some examples, the wearable device 105 may include various types of personal electronic devices and "smart" clothing, in which clothing may be integrated with a vital signs monitoring assembly (e.g., including the one or more monochromatic light sources 110, polychromatic light source 115, spectral sensor 120, and one or more sensors 140). For example, suitable wearable devices 105 may include, without limitation, a smart watch, smart glasses, a temporarily attachable device, an implantable device, shirts, headwear including headbands and hats, footwear including socks and shoes, pants, undergarments, helmets, wristband devices such as fitness trackers, necklaces, rings, and bracelets, among a growing number of wearable devices which may be held, carried, or worn in close proximity to the body of the patient 145. For example, a wrist band device may be configured to be secured to the wrist of the patient 145. The wrist band device may be configured such that when it is worn by the patient 145, one or more of the polychromatic light source 115, such as a white LED, one or more monochromatic light sources 110, such as a red & IR LED, and the spectral sensor 120 are operatively coupled to the wrist of the patient 145. Similarly, in some embodiments, the wearable device 105 may be a glove configured to cover all or part of the hand of the patient 145. The glove may be configured such that when it is worn by the patient 145, one or more of the polychromatic light source 115, one or more monochromatic light sources 110, and the spectral sensor 120 is operatively coupled to the hand of the patient 145. In some embodiments, the wearable device 105 may be a headband device configured such that when it is worn by the patient 145, one or more of the polychromatic light source 115, one or more monochromatic light sources 110, and spectral sensor 120 is operatively coupled to a forehead of the patient 145.

In some embodiments, the wearable device 105 may be a temporarily attachable device configured to attach to a patient 145. Attachment may be achieved, for example, via adhesive. The temporarily attachable device may be configured to be attached to the chest, back, or any other area of the patient's 145 body sufficiently large to accommodate the temporarily attachable device. An example of one such embodiment is described in greater detail below, with respect to FIG. 2.

In various embodiments, the components of the wearable device 105 may be arranged according to a part of the patient 145 to which the wearable device 105 is to be worn over and/or attached, and the specific form factor of the wearable device 105 to accommodate the respective part of the patient 145. For example, in one configuration of a glove, the polychromatic light source 115 and/or one or more monochromatic light sources 110 may be adjacently positioned to the spectral sensor 120 within a threshold proximity of each other. In various embodiments, the threshold proximity may be be a distance from the spectral sensor 120 that an illuminated area of the perfused tissue of the hand may be detectable by the spectral sensor 120. Alternatively, using the same example, in some embodiments, the polychromatic light source 115 and one or more monochromatic light sources 110 may be positioned on an opposite side of a finger from the spectral sensor.

In various embodiments, the wearable device 105 may be configured to modify an algorithm for determining the vital signs based, at least in part, on the area of the body in contact with the wearable device 105. In some embodiments, this may include determination of the type of wearable device 105 (e.g., a wristband device vs. a headband device). In some further embodiments, the wearable device 105 may be configured to determine a part of the body with which contact is made via the one or more sensors.

In various embodiments, the wearable device 105 may further include logic configured to control various functions of the wearable device 105. The logic may be implemented as hardware, software, or both hardware and software. For example, in some embodiments, logic may include a calibration circuit as described in the '477 application. In some embodiments, the logic may include a set of instructions executable by the hardware of the wearable device 105, such as the processor 125, and may be stored in system memory 130 or other storage device. Thus, the logic may, at least partially, be included as part of a software program or application executable by the processor 125 of the wearable device 105. In other embodiments, the logic may include dedicated hardware, which may also include software. Thus, in some examples, the logic may include, without limitation, an embedded system within the mobile device, such as a field programmable gate array (FPGA), system on a chip (SoC), or application specific integrated circuit (ASIC).

Accordingly, in various embodiments, the wearable device 105 may be configured to measure the vital signs of a patient 145. As previously described, vital signs of the patient may include, without limitation, a blood oxygen saturation (e.g., peripheral capillary oxygen saturation (SpO2)), heart rate, blood components (e.g., hemoglobin count and/or concentration, carbon monoxide concentration, etc.), or other physiological parameters (e.g., pulse, heart rate, etc.). In various embodiments, the wearable device 105 may be configured to emit light of at least two wavelengths towards perfused human tissue at various sites of the body of the patient 145. In further embodiments, one or more monochromatic light sources 110, such as red & IR LEDs, may be used by the wearable device 105 to illuminate the body of the patient 145. In still further embodiments, a combination of the one or more monochromatic light sources 110 and polychromatic light source 115 may be used by the wearable device 105 to illuminate the body of the patient 145. In some embodiments, the wearable device 105 may, via an on-board computer, such as an on-board controller including the processor 125 and/or memory 130, may be configured to cause polychromatic light source 115, such as a white LED, to illuminate the body of the patient 145. For example, the on-board controller, such as processor 125 and memory 130, may include driver circuitry and/or logic for driving the polychromatic light source 115 and/or one or more monochromatic light sources 110.

In various embodiments, the once the tissue has been illuminated by a source signal from the polychromatic light source 115, one or more monochromatic light sources 110, or both polychromatic light source 115 and one or more monochromatic light sources 110, the wearable device 105 may be configured to receive a reflected signal from the body of the patient 145, or in alternative embodiments, a transmitted signal through the body of the patient 145. For ease of description, both transmitted and reflected signals will be referred to as the reflected signal in this description, or alternatively "the resultant signal." The reflected signal may result from the source signal (e.g., incident light) being reflected (or transmitted through) by the body of the patient 145. For example, in various embodiments, the body of the patient 145 may, at least partially, absorb one or more component wavelengths of the source signal. Thus, the differences in wavelengths between the source signal and the reflected signal may indicate different characteristics of the perfused tissue (e.g., fluids in the tissue).

Accordingly, the wearable device 105 may be configured to receive the reflected signal from body of the patient 145 via one or more photodetectors, such as the spectral sensor 120. In various embodiments, the spectral sensor 120 may include one or more photodetectors configured to measure light power at one or a range of wavelengths. Accordingly, in various embodiments, the wearable device 105 may be configured to determine spectral properties of the reflected signal based on inputs from the spectral sensor 120. For example, the determination of spectral properties may, in some embodiments, include determination of a transmission spectrum and/or a spectral power distribution.

In various embodiments, based on the spectral properties of the reflected signal, the wearable device 105 may be configured to determine one or more vital signs of the patient 145. For example, in some embodiments, the vital signs monitoring assembly of the wearable device 105 may be configured to cause the polychromatic light source 115 to illuminate the tissue of a patient 145 with a broad-spectrum source signal. The resulting reflected signal may be received by the spectral sensor 120. The reflected signal may then further be processed, for example, by the processor 125, to determine a transmission spectrum and/or spectral power distribution of the reflected signal, indicative of transmission wavelengths with the most optical intensity and/or optical power.

In some embodiments, using a polychromatic light source 115, events that would normally invalidate data derived from one or more monochromatic light sources 110, such as movement, may be corrected and/or replaced. Such processes are described in greater detail with respect to FIG. 3 below.

In some embodiments, the reflected signal may be processed to obtain a pulse waveform proportional to the arterial and venous pulse of a body. For example, in some embodiments, the pulse waveform may be determined based on an absorption and/or reflectance of various wavelengths of the source signal by the tissue of the patient 145 (e.g., comparing the source signal with the reflected signal), based on the spectral transmission and/or absorption properties of oxygenated (arterial) bhO2 and deoxygenated (venous) hemoglobin (Hgb) molecules. Additional algorithms for determining vital signs are discussed in further detail in the '477 application.

In yet further embodiments, the wearable device 105 may be configured to determine a context in which the vital signs are being determined. For example, a context may include, without limitation, an area of the body of the patient 135, or characteristics specific to the patient 135, from which signals are measured by the vital signs monitoring assembly. For example, the wearable device 105 may be configured to determine whether the sensor is receiving signals reflected from a specific body parts such as, without limitation, the hands, feet, arms, legs, wrists, elbows, neck, chest, back, or head. In some further examples, the wearable device 105 may be configured to determine further characteristics, such as height, weight, skin tone, medical conditions, or other information that may affect the received signal. Accordingly, in some embodiments, context may be determined by the wearable device 105 based on inputs from the one or more sensors, to determine characteristics specific to the patient 135. Alternatively, the wearable device 105 may be deployed with an initial configuration based on the type of device of the wearable device. For example, a wearable device such as a headband may be configured to include algorithms for determining vital signals based on a reflected signal from a forehead or scalp, whereas a wristband device may be configured to include determine vital signals based on reflected signals from a wrist or hand.

In further embodiments, the wearable device 105 may be configured to adjust to the reflected signal it receives automatically, as described in further detail in the '477 application. For example, the wearable device 105 may be configured to perform a calibration process. In some embodiments, the wearable device 105 may further include a calibration circuit for calibrating to its environment. Accordingly, in various embodiments, the wearable device 105 may be configured to adjust its measurements of vital signs based on the determination of the context.

In some embodiments, the wearable device 105 may coupled to a network 150. The wearable device 105 may be configured to communicate with various remote devices, such as a provider system 140 or a user device 145. Accordingly, in some embodiments, the wearable device 105 may further include a communications subsystem, configured to communicate with remote devices, both directly or via network 150. Accordingly, in some embodiments, the provider system 140 may be a computer system associated with a healthcare provider. By maintaining communication with the wearable device 105, a healthcare provider may be able to monitor the patient 135 via the wearable device 105. Alternatively, a patient 135 may decide to contact their healthcare provider and provide information from the wearable device to the provider system 140. Similarly, data from the wearable device 105 may be accessed by a user, such as the patient 135, via user device 145 through a direct connection (e.g., a Bluetooth, or other wireless or wired connection), or via the network 150.

Figure 2:
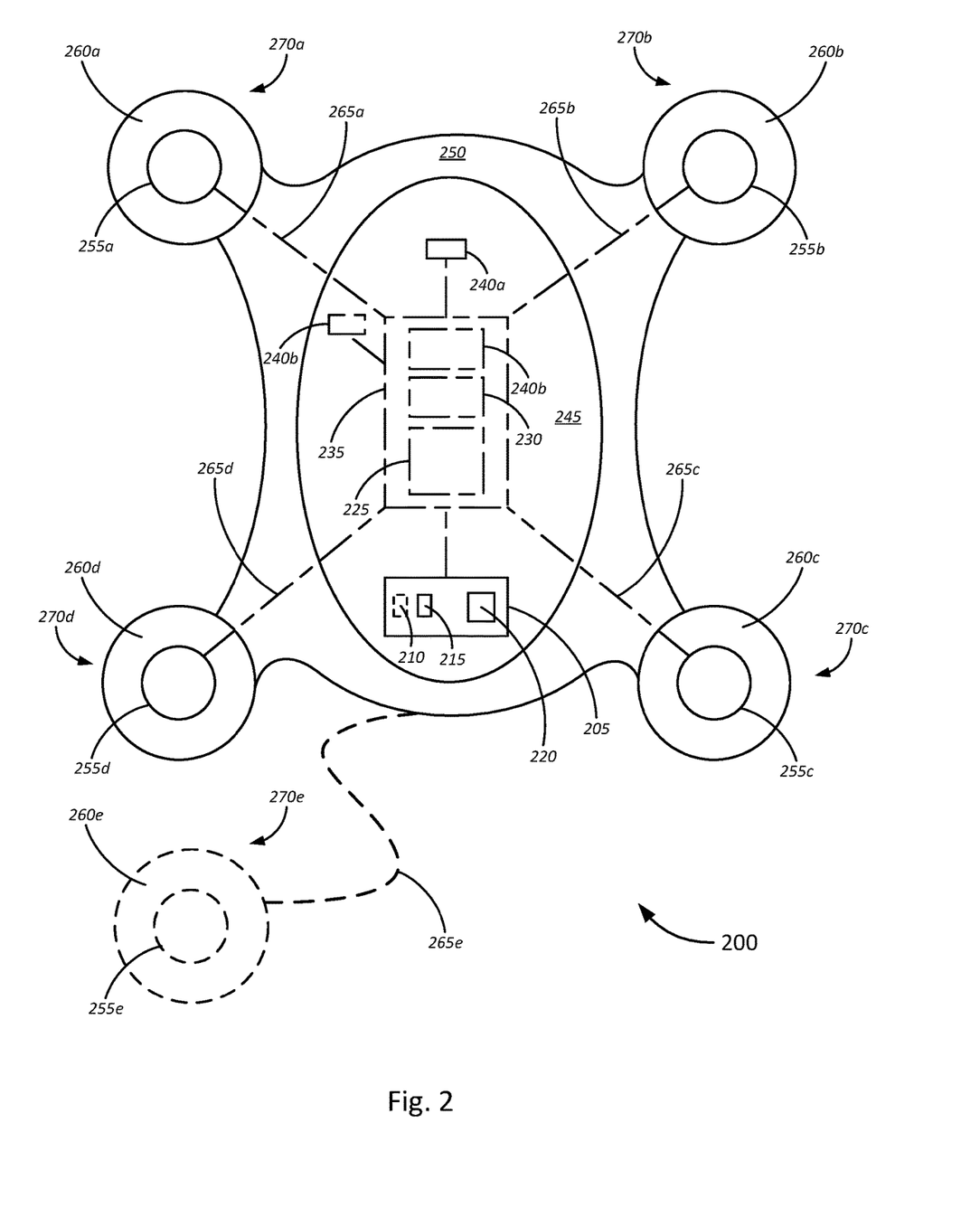
FIG. 2 is a schematic diagram of an example configuration for a wearable vital signs monitor, in accordance with various embodiments.

FIG. 2 is a schematic diagram of an example configuration for a wearable vital signs monitor 200. The wearable vital signs monitor 200 may include a monitoring assembly 205 further including one or more monochromatic light source 210, polychromatic light source 215, and spectral sensor 220, an on-board computer 235 including processor 225, and memory 230, additional sensor(s) 240b, and temperature sensor 240a. In some embodiments, one or more of the vital signs monitoring assembly 205, on-board computer 235, and sensors (including temperature sensor 240a and additional sensor(s) 240b) may be positioned or embedded within an adhesive material 245. The adhesive material 245 may therefore define a central adhesive area of the wearable vital signs monitor 200. The wearable vital signs monitor 200 may further include an outer shell 250 surrounding the various components of the wearable vital signs monitor 200.

The wearable vital signs monitor 200 may further include a first ECG sensor 270a, second ECG sensor 270b, third ECG sensor 270c, fourth ECG sensor 270d, and remote ECG sensor 270e (collectively, "ECG sensors 270"). The first ECG sensor 270a may include a first electrode 255a positioned or surrounded by a first removable adhesive 260a, and a first electrode lead 265a. Similarly, each of the second, third, fourth, and remote ECG sensor 270b-270e may respectively include a second, third, fourth, and remote electrodes 255b-255e, second, third, fourth, and remote removable adhesives 260b-260e, and second, third, fourth, and remote electrode leads 265b-265e.

It should be noted that the components of the wearable vital signs monitor 200 are schematically illustrated in FIG. 2, and that a variety of hardware configurations are possible in accordance with various embodiments.

In various embodiments, the wearable device 200 may be coupled to a patient. The monitoring assembly 205 may be positioned on the wearable device 200 so as to be operatively coupled to the patient. The monitoring assembly 205 may, in turn, be coupled to an on-board computer 235. The on-board computer 235 may include a processor 225, memory 230, and in some example, one or more sensors 240b. The Wearable device 205 may further include a temperature sensor 240a, coupled to the on-board computer 235, and positioned to further be operatively coupled with the skin and/or other tissue of a patient. Each of the monitoring assembly 205, on-board computer 235, and temperature sensor 240a may be positioned on and/or embedded within an adhesive material 245. The adhesive material 245, in turn, may be surrounded by an outer shell 250. ECG sensors 270 may further be coupled to the on-board computer 235 via respective electrode leads 265a-265e. The wearable device 200 and/or the outer shell 250 may include the first through fourth ECG sensors 270a-270b, which, in some embodiments, may be disposed, respectively, at a top left, top right, bottom left, and bottom right corners of the wearable device 200.

FIG. 2 schematically depicts an elevation view of a patient-facing side of the wearable device 200. Accordingly, features that are not visible, embedded within, or on a side facing away from the patient are depicted in alternating long-short dashed lines. Features that may be optionally included in various embodiments, such as remote ECG sensor 270e, are depicted in dashed line.

In some embodiments, the wearable device 200 may be configured to be attached to a chest of the patient. Accordingly, the first ECG sensor 270a, being located at the top left corner, may be associated with an ECG taken at a left arm of the patient, and the second ECG sensor 270b, located at the top right corner, may be associated with an ECG taken at a right arm of the patient. The third ECG sensor 270c may act as a reference ECG, while the fourth ECG sensor 270d may provide an ECG as measured from the sternum, or alternatively, the left leg of a patient. A remote ECG sensor 270e, which may be placed at a desired location of the patient and may be physically separate from the outer shell 250 of the wearable device 200. Thus, the remote ECG sensor 270e may be coupled to wearable device 200, and specifically the on-board computer 235, via the remote electrode lead 265e.

Each of the ECG sensors 270a-270e may include a respective electrode 255a-255e, each respective electrode 255a-255e respectively surrounded by a removable adhesive 260a-260e. In various embodiments, the removable adhesive 260a-260e may keep the respective electrode 255a-255e attached to the patient. In some embodiments, the removable adhesive 260a-260e may be removed, relocated, and/or reattached by the patient or healthcare provider.

In some embodiments, the removable adhesive 260a-260e may include various types of adhesives, such as, without limitation, an adhesive glue or gel, as known to those skilled in the art, that is suitable for use in the local environment of the patient's skin and/or tissue. Suitable adhesive gels may include, for example, and without limitation, a hydro-colloid gel. Similarly, the adhesive material 245, centrally located on the wearable device 200, may be configured to be removably attached to the patient. In some embodiments, the adhesive material 245 may also include an adhesive medical glue, or a gel-adhesive, such as a hydro-colloid gel.

In various embodiments, the wearable device 200 may further include one or more sensors, including a temperature sensor 240a, and one or more additional sensors 240b. The temperature sensor 240a may include, without limitation, a thermometer (e.g., resistance thermometer, IR thermometer), thermistor, thermocouple, or other suitable temperature sensors as known to those skilled in the art. In some embodiments, one or more additional sensors 240b may be included as part of the on-board computer 235, or external to the on-board computer 235. The one or more additional sensors 240b may include, without limitation, motion sensors (e.g., acoustic, IR, microwave, ultrasonic, video), accelerometers, position sensors (e.g., gyroscopes, Bluetooth position sensors, RF-based position sensors), acoustic sensors (e.g., microphones), a glucose sensor, and other sensors as appropriate.

In various embodiments, one or more of the outer shell 250, adhesive material 245, and removable adhesive 260a-260e may be configured to accommodate movement and motion of a patient. Accordingly, the wearable device 200, including one or more of the outer shell 250, adhesive material 245, and removable adhesive 260a-260e, may be configured to be flexible such that movement of the patient is accommodated while remaining operatively attached to the patient. Moreover, in some embodiments, each of the first through fourth ECG sensors 270a-270d may be configured to move and/or bend independently from one another.

In various embodiments, the electrodes 255a-255e may be configured to be spaced with a distance and positioning that is based, at least in part, on a measurement of a P wave of the patient. Accordingly, in some embodiments, a distance between any point of two of the electrodes 255a-255e may be 90 mm or greater. For example, in some embodiments, the distance between any two adjacent electrodes may be 90 mm or greater. For example, in some embodiments, the distance between the first electrode 255a and second electrode 255b may be 90 mm. In other embodiments, the longest distance between any two electrodes may be 90 mm. For example, in some embodiments, the distance between the first electrode 255a and third electrode 255c may be 90 mm. In this wave, a P wave of the patient may be measured, as will be apparent to those skilled in the art.

Figure 3:
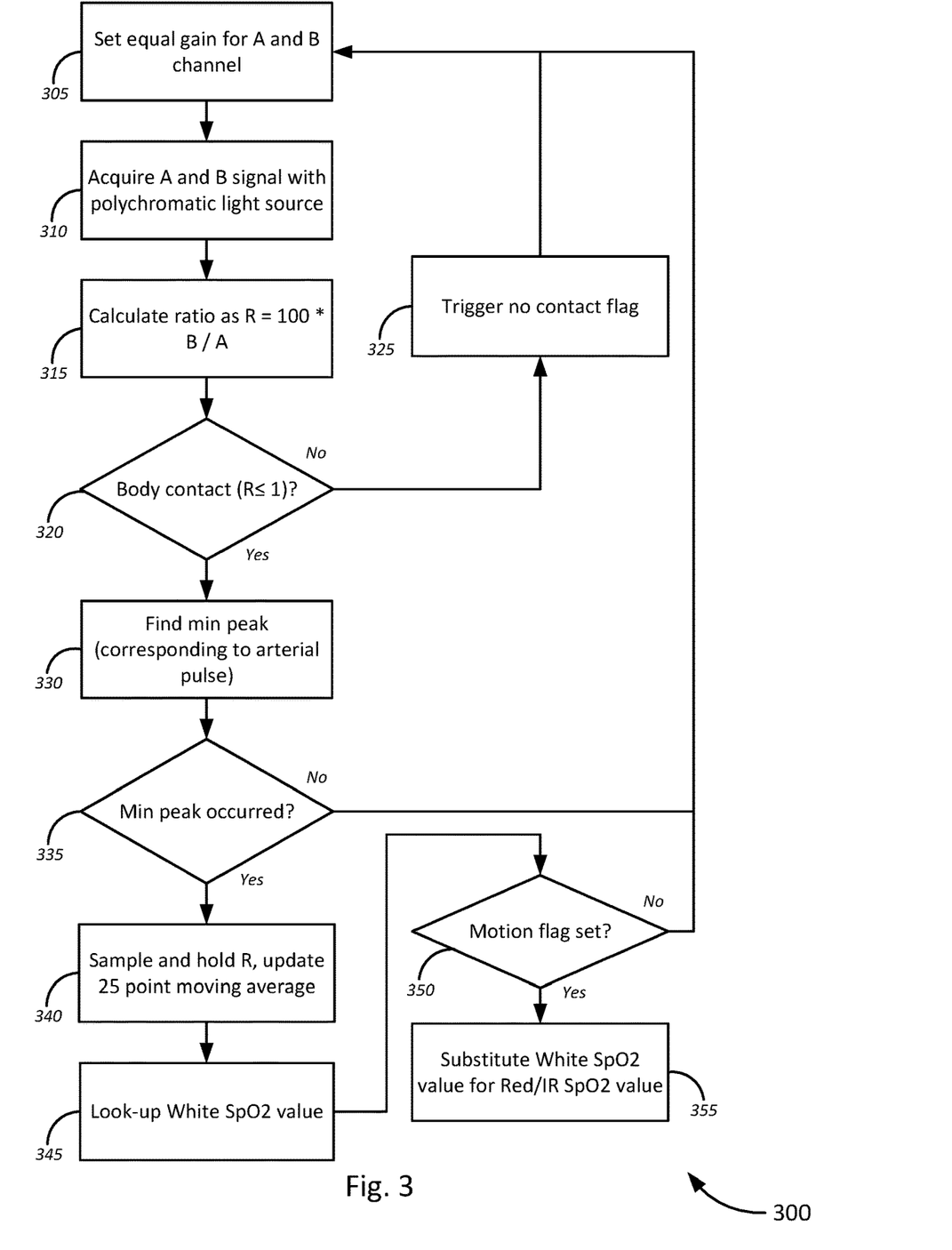
FIG. 3 is a flow diagram of a method for determining SpO2 based on a polychromatic light source, in accordance with various embodiments.

FIG. 3 illustrates a method 300 for determining a white SpO2 based on a polychromatic light source, as related to system 100 and system 200. While in various embodiments, processes may be described in a certain order for purposes of illustration, it should be appreciated that certain processes may be reordered and/or omitted within the scope of various embodiments. Moreover, while the methods described can be implemented by (and, in some cases, were described with respect to) the system 100 and system 200 of FIGS. 1 & 2 (or components thereof), these methods may also be implemented using any suitable hardware implementation. Similarly, while the system 100 and system 200 of FIGS. 1 & 2 (and/or components thereof) can operate according to the methods described and/or the techniques described in the '477 application (e.g., by executing instructions embodied on a computer readable medium), the systems 100, 200 may also operate according to other modes of operation and/or perform other suitable procedures.

In various embodiments, the method 300 begins, at block 305, by setting an equal gain for A and B channels of one or more light sensors. In various embodiments, the one or more photodetectors, such as a spectral sensor as previously described. In some embodiments, the spectral sensor may be configured to measure spectral power distribution and/or intensity of light at one or more wavelengths. In some embodiments, each of the A and B channels may be associated with spectral power and/or intensity at a respective wavelength and/or range of wavelengths.

At block 310, A and B channel data is acquired using a polychromatic light source. In some embodiments, A and B channel data may be gathered by illuminating the patient with the polychromatic light source one or more times. For example, in some embodiments, the polychromatic light source may be configured to be turned on and off at 30 times a second. Accordingly, the polychromatic light source may be strobed and/or pulsed at 30 Hz.

The method 300 continues, at block 315, by determining a ratio of the two signals as $R=100*B/A$. The ratio may be indicative of a baseline measurement of the average spectral absorption and changes in spectral absorption of the patient tissue during an arterial pulse. At decision block 320, the method 300 continues by determining whether the sensor is in contact with the body of the patient. In some embodiments, this may be determined based on the calculated ratio R. If R is less than or equal to 1, then it may be determined, by the wearable device, whether one or more of the polychromatic light source, spectral sensor, or the wearable device itself is in contact with he body of the patient. If it is determined that there is no body contact, at block 325, a no contact flag may be triggered by the wearable device. The method 300 may then return to block 305, where gain for both A and B channel data is reset to be equal. If it is determined that body contact is present, the method 300 continues, at block 330, to find a minimum peak signal corresponding to an arterial pulse. At decision block 335, it is determined whether a minimum peak signal has occurred. If it is determined that a minimum peak has not occurred (e.g., an arterial pulse has not been detected or has not yet occurred), the method 300 returns to block 305, and gain for both A and B channels is reset to be equal, and A and B channel data is re-acquired (block 310) and the ratio R is recalculated (block 315).

If, at decision block 335, a minimum peak is determined to have occurred, the method 300 continues, at block 340, by sampling and holding the ratio R. Using the sampled and held R, a moving average of the previous 25 sampled and held R values will be updated. At block 345, a white (e.g., polychromatic) light determined SpO2 value is looked up in a lookup table (such as the lookup table of FIG. 4), based on one or more of the sampled and held R value, or the moving average of the previous 25 sampled and held R values.

At decision block 350, it is determined whether a motion flag has been set. In various embodiments, the wearable device may include a motion sensor configured to determine whether the patient has moved. If movement has been detected (e.g., a motion flag set), at block 355, SpO2 values derived from monochromatic light sources, such as red and/or IR LEDs, will be substituted with white SpO2 values determined using the polychromatic light source. In various embodiments, movement of the patient may make it impossible to accurately calculate SpO2 of the patient based on monochromatic light sources. Accordingly, if a motion event occurs, the wearable device will rely on a polychromatic light source derived SpO2 value (e.g., white SpO2). If a motion flag has not been set, the method 300 returns to block 305, in which gain for channels A and B are reset to be equal.

Figure 4:
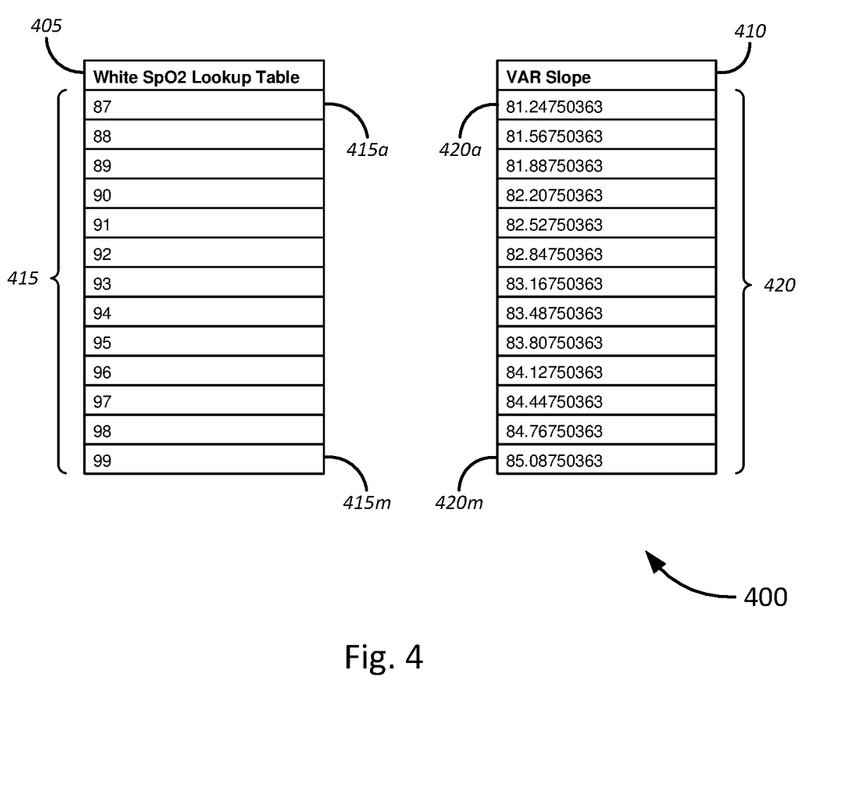
FIG. 4 is a lookup table for obtaining vital signs measurements in a wearable vital signs monitor, in accordance with various embodiments.

FIG. 4 illustrates lookup tables 400 for obtaining vital signs measurements in a wearable vital signs monitor, in accordance with various embodiments. The lookup tables may include a white SpO2 lookup table 405 including a plurality of blood oxygen saturation values 415, and a VAR slope table 410 including a plurality of R values 420. Accordingly, a first R value 420a, corresponding to an R value of 81.24750363 may correspond to a first SpO2 value 415a of 87% blood oxygen saturation. A $13^{th}$ R value 420m of 85.08750363 may correspond to the 13th SpO2 value 415m of 99% blood oxygen saturation. Accordingly each respective entry of the VAR slope table 410 may correspond to a respective entry of the white SpO2 lookup table 405.

Accordingly, SpO2 levels, derived from the polychromatic light source using the ratio R between A and B channels may be determined based on the lookup tables 400 as described above. In further embodiments, different lookup tables and lookup table values may be utilized based on a context for the wearable device (e.g., an area of the body, or a characteristic of the patient). Accordingly, while embodiments of the wearable device may be configured to utilize the lookup tables 400, it is to be appreciated that in further embodiments, the wearable device may be configured to modify and/or use different lookup tables. In some embodiments, one or more lookup tables may be stored by the wearable device on, for example, an on-board computer or storage device. In some embodiments, the one or more lookup tables may be stored on a remote system, such as a separate, dedicated signal processing computer, server, database, or other remotely located device. Accordingly, the storage location of the lookup table may vary in different embodiments.

Figure 5:
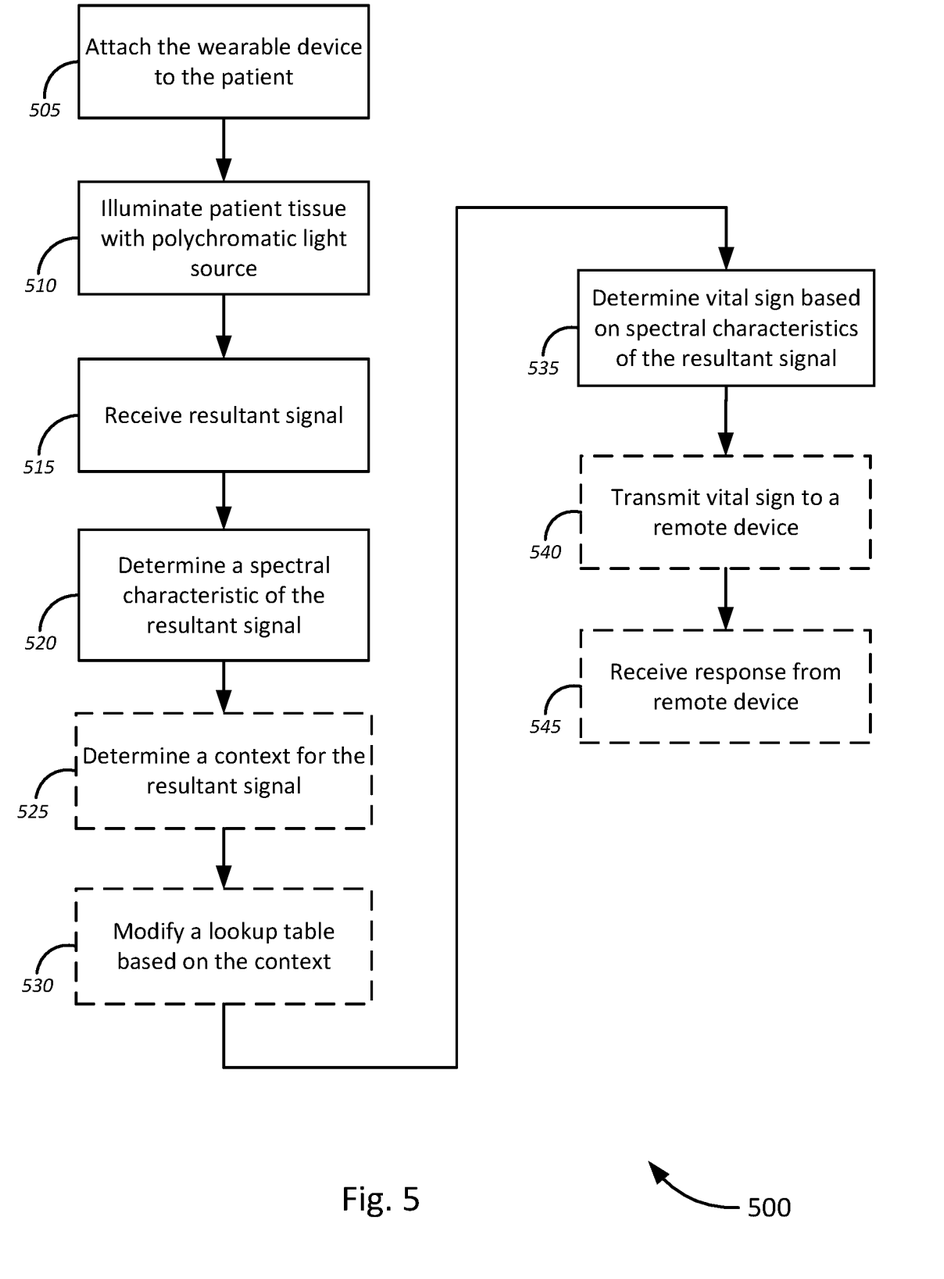
FIG. 5 is a flow diagram of a method of utilizing a wearable vital signs monitor, in accordance with various embodiments.

FIG. 5 is a method 500 for utilizing the wearable device, according to various embodiments. While in various embodiments, processes may be described in a certain order for purposes of illustration, it should be appreciated that certain processes may be reordered and/or omitted within the scope of various embodiments. Moreover, while the methods described can be implemented by (and, in some cases, were described with respect to) the system 100 and system 200 of FIGS. 1 & 2 (or components thereof), these methods may also be implemented using any suitable hardware implementation. Similarly, while the system 100 and system 200 of FIGS. 1 & 2 (and/or components thereof) can operate according to the methods described and/or the techniques described in the '477 application (e.g., by executing instructions embodied on a computer readable medium), the systems 100, 200 may also operate according to other modes of operation and/or perform other suitable procedures.

The method 500 begins, at block 505, the wearable device may be attached to the patient. For example, as previously described with respect to FIG. 2, the wearable device may be positioned such that one or more of the polychromatic light source, spectral sensor, and/or one or more other sensors are operably coupled to the patient. In some embodiments, the wearable device may be positioned to be in contact with at least one of a wrist, palm, back of a hand, arm, chest, forehead, or earlobe of the patient.

The method 500 may continue, at block 510, by illuminating the perfused tissue of a body of a patient with the polychromatic light source. In some embodiments, perfused tissue may include any tissue of the patient through which blood may be flowing. Illuminating the perfused tissue may include transmitting, directing, or otherwise providing light, from the polychromatic light source, to the surface of the perfused tissue, or alternatively, through the perfused tissue.

At block 515, a resultant signal may be received by a spectral sensor of the wearable device. As previously described, with respect to FIGS. 1 and 2, the resultant signal may be a signal reflected by and/or received through the perfused tissue. At block 530, a spectral characteristic of the resultant signal may be determined. Spectral characteristics may include, without limitation, an optical power, intensity, or a spectral power distribution (e.g., power per unit area per unit wavelength). In some embodiments, for example, power and/or intensity of the resultant signal may be measured at two or more wavelengths (e.g., a first wavelength and a second wavelength). In some embodiments, the two or more wavelengths may not be a singular wavelength, but rather include a narrow bandwidth measurement over a range of wavelengths centered around a first wavelength and a second wavelength. Accordingly, in various embodiments, determining the spectral characteristics of the resultant signal may include determining a power spectral density or intensity of the resultant signal at a first wavelength and a second wavelength. The first wavelength may correspond to a first channel, such as channel A described above with respect to FIG. 3. Second wavelength may correspond to a second channel, such as channel B described above with respect to FIG. 3.

At optional block 525, the method 500 may further include determining a context of the resultant signal, and at optional block 530, modifying a lookup table based on the context. As previously described, determining a context for the resultant signal may include, without limitation, determining an area of the body of the patient that is illuminated by incident light from the polychromatic light source. For example, in some embodiments, the context may be indicative that the wearable device was attached, without limitation, to a wrist, palm, back of a hand, arm, chest, forehead, or earlobe of the patient. Accordingly, based on the context for receiving a resultant signal, a corresponding lookup table may be modified. As previously described, in some embodiments modification of a lookup table may include modifying one or more values stored within a lookup table, or a relationship between one or more values of the lookup table. In other embodiments, modification of the lookup table may include selection of one or more lookup tables to be utilized according to the determined context.

The method 500 continues, at block 535, by determining a vital sign based on spectral characteristics of the resultant signal. As previously described, a vital sign may include, without limitation, SpO2, heartrate, blood components, or other physiological parameters. Determining a vital sign, such as SpO2, may be determined based on measured spectral characteristics of the resultant signal as previously described with respect to FIG. 3. At optional block 540, the vital sign may be transmitted to a remote device. As previously described, the wearable device may include a communications subsystem configured to allow the wearable device (e.g., an on-board computer of the wearable device) with a communication network via which the wearable device may communicate with one or more remote device. Alternatively, the wearable device may be configured to communicate directly with one or more remote devices via a wired and/or wireless communication medium. At optional block 545, the wearable device may further be configured to receive a response from the remote device indicative of receipt of the determined vital sign from the wearable device. The response may include for example, and without limitation, instructions to determine one or more other vital signs, monitor one or more other sensors, adjust one or more lookup table values, alert the patient, etc.

Figure 6:
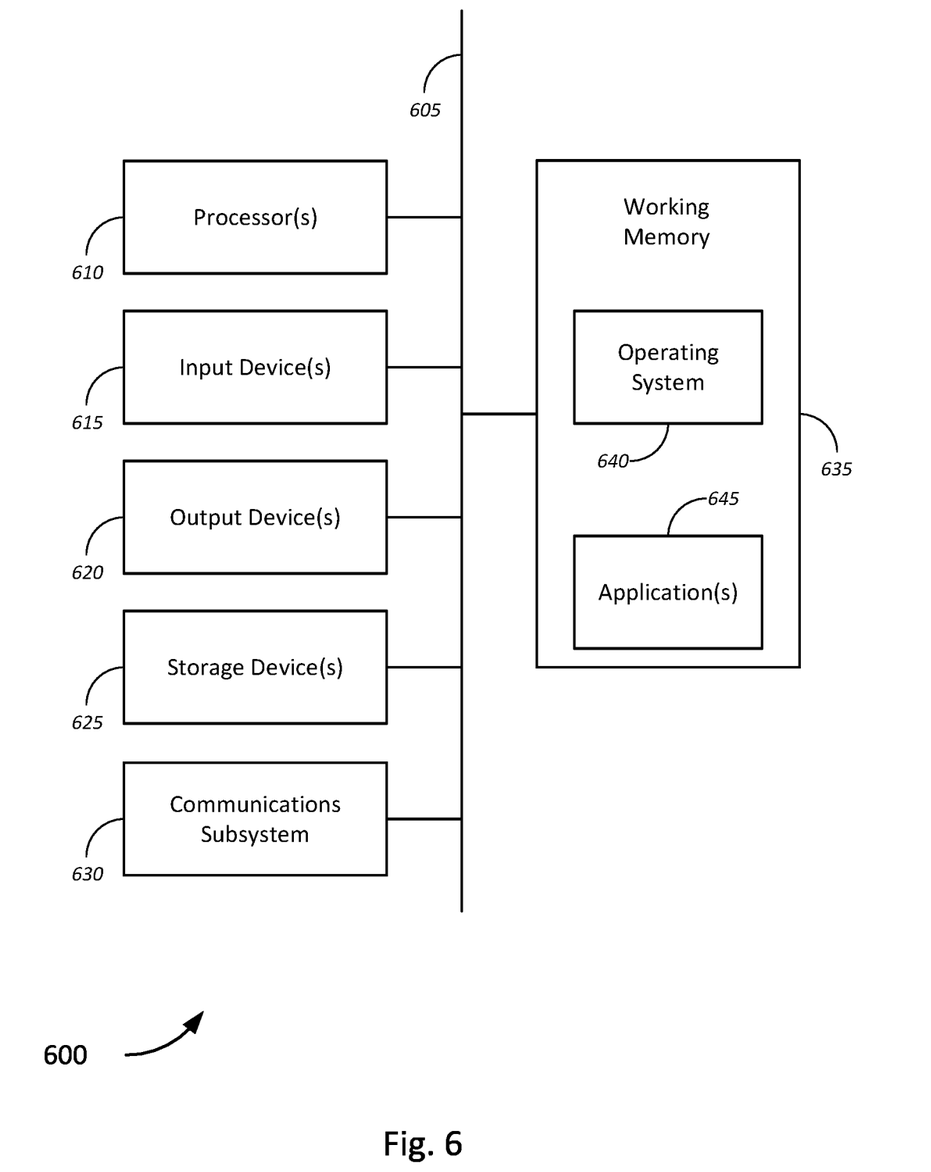
FIG. 6 is a schematic block diagram of a computer system for a wearable vital signs monitor, in accordance with various embodiments.

FIG. 6 is a schematic illustration of one embodiment of a computer system 600 configured to perform the methods provided by various other embodiments, as described herein. It should be noted that FIG. 6 is meant only to provide a generalized illustration of various components, of which one or more (or none) of each may be utilized as appropriate. FIG. 6, therefore, broadly illustrates how individual system elements may be implemented in a relatively separated or relatively more integrated manner.

The computer system 600 is shown comprising hardware elements that can be electrically coupled via a bus 605 (or may otherwise be in communication, as appropriate). The hardware elements may include one or more processors 610, including without limitation one or more general-purpose processors and/or one or more special-purpose processors (such as digital signal processing chips, graphics acceleration processors, and/or the like); one or more input device(s)

615, which may include, without limitation, one or more sensors, touchscreens, microphones, keyboards, computer mice, cameras, and other interface devices; one or more output devices 620, which may include, without limitation, a display, lights (e.g., LEDs), speakers, other indicators such as a vibrating element; one or more storage devices 625, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 600 might also include a communications subsystem 630, which can include without limitation a modem, a network card (wireless or wired), an infra-red communication device, a wireless communication device and/or chipset (such as a Bluetooth™ device, an 802.11 device, a Wife device, a WiMax device, a WWAN device, cellular communication facilities, etc.), and/or the like. The communications subsystem 630 may permit data to be exchanged with a network (such as the network described below, to name one example), with other computer systems, and/or with any other devices described herein. In many embodiments, the computer system 600 will further comprise a working memory 635, which can include a RAM or ROM device, as described above.

The computer system 600 also may comprise software elements, shown as being currently located within the working memory 635, including an operating system 640, device drivers, executable libraries, and/or other code, such as one or more application programs 645, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 625 described above. In some cases, the storage medium might be incorporated within a computer system, such as the system 600. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the computer system 600 and/or might take the form of source and/or installable code, which, upon compilation and/or installation on the computer system 600 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 600) to perform methods in accordance with various embodiments of the invention. According to a set of embodiments, some or all of the procedures of such methods are performed by the computer system 600 in response to processor 610 executing one or more sequences of one or more instructions (which might be incorporated into the operating system 640 and/or other code, such as an application program 645) contained in the working memory 635. Such instructions may be read into the working memory 635 from another computer readable medium, such as one or more of the storage device(s) 625. Merely by way of example, execution of the sequences of instructions contained in the working memory 635 might cause the processor(s) 610 to perform one or more procedures of the methods described herein.

The terms "machine readable medium" and "computer readable medium," as used herein, refer to any medium that participates in providing data that causes a machine to operation in a specific fashion. In an embodiment implemented using the computer system 600, various computer readable media might be involved in providing instructions/code to processor(s) 610 for execution and/or might be used to store and/or carry such instructions/code (e.g., as signals). In many implementations, a computer readable medium is a non-transitory, physical and/or tangible storage medium. Such a medium may take many forms, including but not limited to, non-volatile media, volatile media, and transmission media. Non-volatile media includes, for example, optical and/or magnetic disks, such as the storage device(s) 635. Volatile media includes, without limitation, dynamic memory, such as the working memory 645. Transmission media includes, without limitation, coaxial cables, copper wire and fiber optics, including the wires that comprise the bus 605, as well as the various components of the communication subsystem 630 (and/or the media by which the communications subsystem 630 provides communication with other devices). Hence, transmission media can also take the form of waves (including without limitation radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 610 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 600. These signals, which might be in the form of electromagnetic signals, acoustic signals, optical signals and/or the like, are all examples of carrier waves on which instructions can be encoded, in accordance with various embodiments of the invention.

The communications subsystem 630 (and/or components thereof) generally will receive the signals, and the bus 605 then might carry the signals (and/or the data, instructions, etc. carried by the signals) to the working memory 635, from which the processor(s) 610 retrieves and executes the instructions. The instructions received by the working memory 635 may optionally be stored on a storage device 625 either before or after execution by the processor(s) 610.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A system comprising:
a remote device coupled to a communications network;
a wearable device in communication with the remote device via the communications network, the wearable device configured to be in contact with a body of a patient and determine vital signals of a patient, the wearable device comprising:
a polychromatic light source;
a spectral sensor;
one or more other sensors;
a processor; and
a non-transitory computer readable medium comprising instructions executable by the processor to:
illuminate, via the polychromatic light source, a perfused tissue of the body of the patient;
receive, via the spectral sensor, a polychromatic resultant signal from the body of the patient;
determine a spectral property of the polychromatic resultant signal as measured by the spectral sensor, wherein the spectral property includes a light power measurement of polychromatic light; and
determine a vital sign of the patient based, at least in part, on a lookup table and the spectral property of the polychromatic resultant signal, wherein the lookup table is indicative of a value of the vital sign,
wherein the instructions are further executable by the processor to:
determine a context for the polychromatic resultant signal based on input from the one or more other sensors, wherein the context is indicative of an area of the body of the patient illuminated by the polychromatic light source; and
adjust at least one value of the lookup table based at least in part on the context determined for the polychromatic resultant signal based on the input from the one or more other sensors.

2. The system of claim 1, wherein determining the context for the polychromatic resultant signal includes determining whether the perfused tissue illuminated by the polychromatic light source is a wrist, palm, back of a hand, arm, chest, forehead, or earlobe.

3. The system of claim 1, wherein the wearable device is a wrist band, wherein the perfused tissue of the body illuminated by the polychromatic light source is a wrist of the patient.

4. The system of claim 1, wherein the wearable device is a glove, wherein the perfused tissue of the body illuminated by the polychromatic light source is a hand of the patient.

5. The system of claim 1, wherein the wearable device is a headband, wherein the perfused tissue of the body illuminated by the polychromatic light source is a forehead of the patient.

6. The system of claim 1, wherein the wearable device is an attachable device comprising an adhesive configured to attach the wearable device to the body of the patient, wherein the perfused tissue of the body illuminated by the polychromatic light source includes a chest of the patient.

7. The system of claim 1, wherein the instructions are further executable by the processor to transmit, via the communications network, the vital sign of the patient to the remote device.

8. The system of claim 7, wherein the instructions are further executable by the processor to receive, via the communications network, a response from the remote device to transmitting the vital sign of the patient to the remote device, wherein the response is configured to adjust the at least one value of the lookup table.

9. The system of claim 1, wherein the polychromatic resultant signal is a reflected signal from the body of the patient.

10. The system of claim 1, wherein the polychromatic resultant signal is a transmissive signal from the body of the patient, wherein the polychromatic resultant signal is received through the body of the patient.

11. An apparatus comprising:
a polychromatic light source;
a spectral sensor;
one or more other sensors;
a processor; and
a non-transitory computer readable medium comprising instructions executable by the processor to:

illuminate, via the polychromatic light source, a perfused tissue of a body of a patient;

receive, via the spectral sensor, a polychromatic resultant signal from the body of the patient;

determine a spectral property of the polychromatic resultant signal as measured by the spectral sensor, wherein the spectral property includes a light power measurement of polychromatic light; and determine a vital sign of the patient based, at least in part, on a lookup table and the spectral property of the polychromatic resultant signal, wherein the lookup table is indicative of a value of the vital sign;

wherein the instructions are further executable by the processor to:

determine a context for the polychromatic resultant signal based on input from the one or more other sensors, wherein the context is indicative of an area of the body of the patient illuminated by the polychromatic light source; and adjust at least one value of the lookup table based at least in part on the context determined for the polychromatic resultant signal based on the input from the one or more other sensors.

12. The apparatus of claim 11, wherein determining the context for the polychromatic resultant signal includes determining whether the perfused tissue illuminated by the polychromatic light source is a wrist, palm, back of a hand, arm, chest, forehead, or earlobe.

13. The apparatus of claim 11, further comprising an adhesive configured to attach to the body of the patient, wherein the perfused tissue of the body illuminated by the polychromatic light source includes a chest of the patient.

14. The apparatus of claim 13, wherein the one or more other sensors includes at least one of a motion sensor, temperature sensor, positional sensor, or an electrode.

15. The apparatus of claim 11, further comprising a wristband configured to attach to the body of the patient, wherein the perfused tissue of the body illuminated by the polychromatic light source includes a wrist of the patient.

16. The apparatus of claim 11, further comprising a device body configured to attach to the body of the patient, wherein the perfused tissue of the body illuminated by the polychromatic light source includes a hand of the patient.

17. A method comprising:

illuminating, via a wearable device, a perfused tissue of a body of a patient with a polychromatic light source;

receiving, via a spectral sensor of the wearable device, a polychromatic resultant signal from the body of the patient;

determining, via an on-board computer of the wearable device, a spectral property of the polychromatic resultant signal, wherein the spectral property includes a light power measurement of polychromatic light;

determining, via the on-board computer of the wearable device, a vital sign of the patient based, at least in part, on a lookup table and the spectral property of the polychromatic resultant signal, wherein the lookup table is indicative of a value of the vital sign;

determining a context for the polychromatic resultant signal based on input from one or more other sensors, wherein the context is indicative of an area of the body of the patient illuminated by the polychromatic light source; and adjusting at least one value of the lookup table based at least in part on the context determined for the polychromatic resultant signal based on the input from the one or more other sensors.

* * * * *